United States Patent
Lee et al.

(10) Patent No.: US 7,208,971 B2
(45) Date of Patent: Apr. 24, 2007

(54) MANUAL PROBE CARRIAGE SYSTEM AND METHOD OF USING THE SAME

(75) Inventors: Sang Bin Lee, Seoul (KR); Dongwook Kim, Pine Brook, NJ (US); Waheed Tony Mall, Waterford, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/905,709

(22) Filed: Jan. 18, 2005

(65) Prior Publication Data

US 2005/0093536 A1     May 5, 2005

Related U.S. Application Data

(63) Continuation-in-part of application No. 10/270,326, filed on Oct. 15, 2002, now Pat. No. 6,847,224.

(51) Int. Cl.
   *G01R 31/34*    (2006.01)
   *G01R 31/02*    (2006.01)
   *G01R 31/26*    (2006.01)

(52) U.S. Cl. ............... 324/772; 324/754; 324/757; 324/765

(58) Field of Classification Search ............... None
   See application file for complete search history.

(56) References Cited

U.S. PATENT DOCUMENTS 3,475,682 A * 10/1969 Bateman et al. ............ 324/127

| | | | |
|---|---|---|---|
| 3,525,041 A * | 8/1970 | Velsink | 324/117 R |
| 4,803,563 A | 2/1989 | Dailey et al. | 358/100 |
| 4,970,890 A | 11/1990 | Jaafar et al. | 73/12 |
| 4,996,486 A | 2/1991 | Posedel | 324/545 |
| 5,252,927 A | 10/1993 | Bruhlmeier et al. | 324/546 |

(Continued)

FOREIGN PATENT DOCUMENTS

EP     1 318 411 A2    11/2003

(Continued)

OTHER PUBLICATIONS

D. B. Paley, "Current Low Power Core Testing Using EL CID;" IEE Colloquium—Understanding your condition monitoring; Apr. 1999.

(Continued)

*Primary Examiner*—Jermele Hollington
(74) *Attorney, Agent, or Firm*—Cantor Colburn LLP

(57) ABSTRACT

A probe support carriage for use during probing an electrical device includes a body, means for supporting and positioning the body, a plurality of flux sensors and a position sensor. The body has a first end and a second end. The plurality of flux sensors are operatively connected to the body. Each flux sensor includes a probe having a core and a coil. The core includes a material having high initial permeability and high resistivity characteristics. The probe is adapted to being supported so that a sensing portion of the core is maintained in a contact-free spaced relationship between a predetermined surface of the electrical device and the sensing portion of the core. The position sensor is adapted to determine position along a longitudinal axis of the electrical device.

20 Claims, 14 Drawing Sheets

U.S. PATENT DOCUMENTS

| | | | |
|---|---|---|---|
| 5,295,388 A | 3/1994 | Fischer et al. | 73/12.09 |
| 5,341,095 A | 8/1994 | Shelton et al. | 324/772 |
| 5,446,379 A * | 8/1995 | Machi | 324/240 |
| 5,446,382 A * | 8/1995 | Flora | 324/232 |
| 5,473,247 A * | 12/1995 | You et al. | 324/227 |
| 5,491,409 A * | 2/1996 | Flora et al. | 324/242 |
| 5,557,216 A | 9/1996 | Dailey et al. | 324/772 |
| 5,701,073 A * | 12/1997 | Baker | 324/117 H |
| 5,990,688 A | 11/1999 | Bourgeois et al. | 324/545 |
| 5,992,241 A * | 11/1999 | Posgay et al. | 324/209 |
| 6,469,504 B1 | 10/2002 | Kliman et al. | 324/228 |
| 6,489,781 B1 | 12/2002 | Kliman et al. | 324/545 |
| 6,756,788 B2 | 6/2004 | Kliman et al. | 324/545 |
| 6,847,224 B2 * | 1/2005 | Lee et al. | 324/772 |
| 6,873,152 B2 * | 3/2005 | Kliman et al. | 324/241 |
| 2003/0117144 A1 | 6/2003 | Sutton | 324/546 |
| 2004/0070404 A1 | 4/2004 | Lee et al. | 324/545 |

FOREIGN PATENT DOCUMENTS

| GB | 2395281 A | 5/2004 |
|---|---|---|
| RU | 2082274 C1 | 6/1997 |

OTHER PUBLICATIONS

D. Bertenshaw et al.; "Application of the EL CID Test with Circulation Currents in Stator Windings;" Inductia, Berlin, Germany Jun. 15th-17th, 2004; pp. 128-134.

V. B. Berezhansky et al.; "Experience with Modified Iron Fault Control Technique for the Stator Cores of Electrical Machines;" Paper SPT EM 05-07-0205 accepted for presentation at the IEEE / KTH Stockholm Power Tech. Conference Stockholm, Sweden, Jun. 18-22, 1995; pp. 108-112.

Moore et al; "Electric Generators: Potential Problems and Recommended Solutions;" [online]; [retrieved on Jul. 25, 2001]; retrieved from the Internet http://www.carilec.org/Assets/Presentations%202001/Moore-Carilec-7-25-01.pdf.

* cited by examiner

FIG. 9
FIG. 10
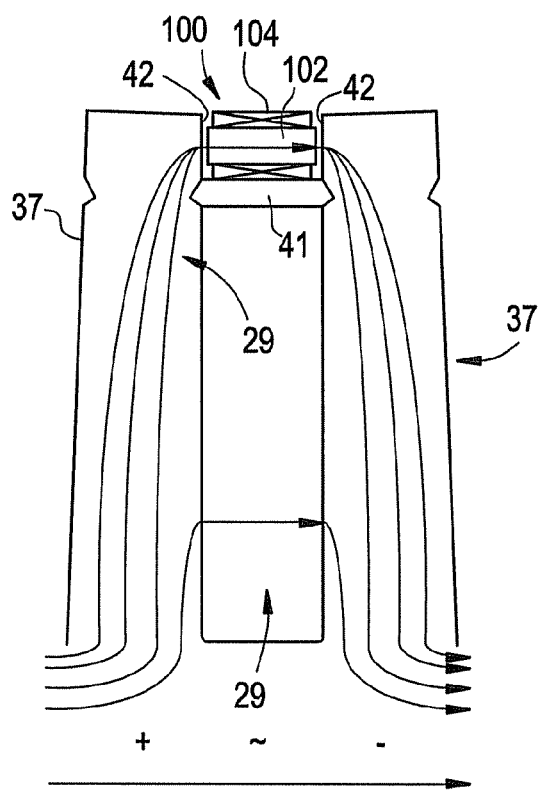
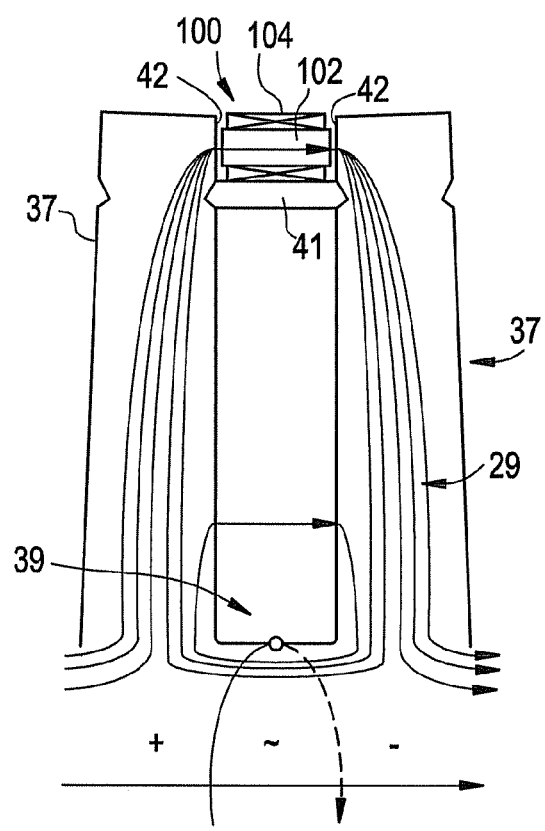

MANUAL PROBE CARRIAGE SYSTEM AND METHOD OF USING THE SAME

CROSS-REFERENCE TO RELATED APPLICATIONS

This application is a continuation-in-part of U.S. application Ser. No. 10/270,326, filed Oct. 15, 2002, now U.S. Pat. No. 6,847,224, which is incorporated herein by reference in its entirety.

BACKGROUND OF THE INVENTION

The invention relates generally to a carriage system for a probe for the diagnosis and monitoring of the operation of an electrical apparatus.

In the field of generating electricity on a commercial scale it is important that elements of the power generating system remain fully functional over their expected working life so that unexpected downtimes and/or catastrophic failures can be avoided. To avoid such problems it is important that elements such as the large stators, which form part of the above-mentioned generating systems are carefully inspected and tested before being sold, after installation at customer site, and during regular periodic maintenance.

The stator core 30 of electric machines (such as schematically depicted in FIG. 1) utilizes thin insulated steel laminations 32 (FIG. 2) to reduce the eddy current flow for higher efficiency operation. The laminations 32 are, as shown in FIG. 2, stacked vertically by placing a dovetail groove 34 of the laminations in the dovetail of a key bar 36, which is attached to a frame of the stator core 30. To hold the laminations together and to prevent lamination vibration, the stator core 30 is axially clamped with a force of about 300–350 psi.

Shorting of the laminations 32 can be caused by manufacturing defects, damage during assembly/inspection/rewind, stator-rotor contact, vibration of loose coil wedges/laminations, foreign magnetic material, etc. If the laminations 32 are shorted for any reason, a larger circulating current is induced in the fault loop that consists of fault-laminations-key bar (see FIG. 2). The typical fault locations 39 are shown in FIG. 3. The circulating fault current 26 increases with the number of shorted laminations and the conductivity between the laminations and the short/key bar. The fault current 26 increases the power dissipation in the stator core and causes localized heating. The hot spots can progress to more severe localized heating and eventually cause burning or melting of the laminations. As a result, the stator bar insulation and windings can also be damaged causing ground current flow through the stator core. Therefore, inter-laminar core faults should be detected and repaired to prevent further damage and to improve the reliability of generator operation.

Various tests have been developed in order to detect imperfections in the stator core 30. The "ring test" relies upon the detection of the eddy current heating caused by the short circuit currents. The stator core 30 is wound with a number of turns (typically less than 10) of electrical cable to form toroidal shaped excitation windings 31 in the manner schematically depicted in FIG. 1. The current level in the windings is chosen such that the flux driven in the stator core 30 is near normal operating levels (approximately 1–1.5 Tesla). The excitation requirement measures several million voltages-amperes (MVA), since several hundred amperes and volts in the coil are needed to achieve the desired flux. The stator core 30 is excited in this manner for several hours.

Thermal imaging cameras are used to find "hot spots" on the inner stator surface. These hot spots indicate the location and severity of the inter-lamination short circuits.

However, short circuits that are located below the surface of the stator teeth 37 and slots are difficult to find, since thermal diffusion causes the surface temperature rise to be diffuse/spread out. Because of the high power levels used in the ring test, personnel cannot enter the bore of the stator core 30 during testing. Further, cables used in the test must be appropriately sized for the required MVA level, which leads to long setup and removal times.

The high flux used in the ring test is a concern because: the high currents (e.g., hundreds of amperes and several thousand volts) needed require a test supply capable of several MVA. Also, the high current and voltage levels require care in the selection and installation of the excitation winding on the generator core because they can obscure parts of the core. Furthermore, because the heating test is run on a core that is deprived of its normal cooling system, excessive heating can lead to core damage. The high current and voltage levels impact operator safety, and as mentioned above, personnel are not allowed to enter the core interior when a ring test is running.

To overcome the shortcomings of the ring test, the "EL CID" (Electromagnetic Core Imperfection Detection) test was developed. This test relies upon detection of the magnetic field caused by the short circuit currents that flow due to inter-lamination short circuits. As in the ring test, the generator core is wound with a number of turns in the manner of a toroid. The current level in the windings is chosen such that the core operates at approximately 4% of the normal operating flux. This corresponds to about a 5 volt/meter electric field induced along the core surface. The current requirement is in the 10–30 ampere range, so that a smaller power supply of several kVA can be used. A magnetic potentiometer, referred to as a Chattock coil 38 after its inventor, is used to sense the magnetic fields produced between two adjacent teeth by the short circuit currents that are induced in the inter-lamination insulation faults.

The Chattock coil 38 (also known as the Maxwell worm or magnetic potentiometer) is used to sense the phase quadrature component of the magnetic field produced by any induced inter-laminar currents. Chattock coil voltages equivalent to those produced by a 100 mA or larger test current are used as the indicator for a severe inter-laminar short for the 4% flux excitation level.

The Chattock coil 38 typically spans the width of two adjacent teeth 37 in the manner shown in FIGS. 4 and 5 and is moved along the surface of the stator either by hand or by a robotic carriage. Because the short circuit current path is largely resistive, the magnetic flux created by the short circuit is in phase quadrature with the exciting flux. The signal from the Chattock coil 38 is combined with a reference signal derived from the excitation current so that phase sensitive detection methods can be used to extract the fault signal from the background noise.

A fully digital EL CID system has been developed. This system exhibits improved noise suppression over the previous analog arrangements. Nevertheless, there are a number of anomalies and distortions, which can arise when performing the EL CID test, and these must be interpreted using knowledge and experience of core construction.

The EL CID test involves exciting the core in a manner similar to that of the ring test, but uses much lower voltage and current levels. A flux of 4–5% is normal. The EL CID test procedure exhibits the following characteristics. The current required for this flux can be obtained from a variable transformer that is supplied from a standard electrical outlet. The induced voltage from this low flux is kept to about 5 volts/meter, so personnel can enter the core during the EL CID test to make observations. The induced currents at this flux are low enough not to cause excessive heating, so additional core damage due to testing is not a concern.

The EL CID test is better able to find inter-laminar faults, which are located below the surface. This is a significant advantage over the ring test that relies upon thermal diffusion from the interior hot spot in order to provide detection. However, the EL CID test can exhibit high noise levels, especially when scanning in the end step region 35 (see FIG. 12). The high noise levels are due to the Chattock coil 38 being located on one side of the EL CID trolley, requiring the trolley to be flipped or carefully positioned at the end step region 35. Additionally, handling the trolley occasionally results in breakage of the fine wire that is wound around the Chattock coil 38.

Thus, it is desirable to develop a probe that is not subject to breakage due to handling and which will also not require flipping in the end step region 35.

BRIEF DESCRIPTION OF THE INVENTION

Exemplary embodiments of the invention include a probe support carriage for use during probing an electrical device. The probe support carriage includes a body, means for supporting and positioning the body, a plurality of flux sensors and a position sensor. The body has a first end and a second end. The plurality of flux sensors are operatively connected to the body. Each flux sensor includes a probe having a core and a coil. The core includes a material having high initial permeability and high resistivity characteristics. The probe is adapted to being supported so that a sensing portion of the core is maintained in a contact-free spaced relationship between a predetermined surface of the electrical device and the sensing portion of the core. The position sensor is adapted to determine position along a longitudinal axis of the electrical device.

Further exemplary embodiments of the invention include a method of detecting an electrical fault in an electrical device. The method includes supporting a plurality of probes on a trolley, maintaining a sensing portion of the solid core in a contact-free, spaced relationship between opposed surfaces of members of the electrical device through which a leakage flux passes, inducing energization of the electrical device to a predetermined level, detecting the leakage flux using each probe at a first position, moving the trolley to a second position with respect to the opposed surfaces and detecting the leakage flux, monitoring a fluctuation in output of each probe and detecting the fault in response to an abnormal leakage flux, and determining an axial position of said trolley within the electrical device. Each probe has a solid core and a coil disposed with the solid core. The predetermined level is lower than a normal operating level.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 9 is a schematic front view showing the deployment of a probe or sensor according to an embodiment of the invention and depicting the leakage flux, which occurs in the absence of a fault.

FIG. 10 is a schematic front view similar to that shown in FIG. 9, but which depicts the situation wherein a fault has occurred and the leakage flux has changed accordingly.

DETAILED DESCRIPTION OF THE INVENTION

Figure 1:
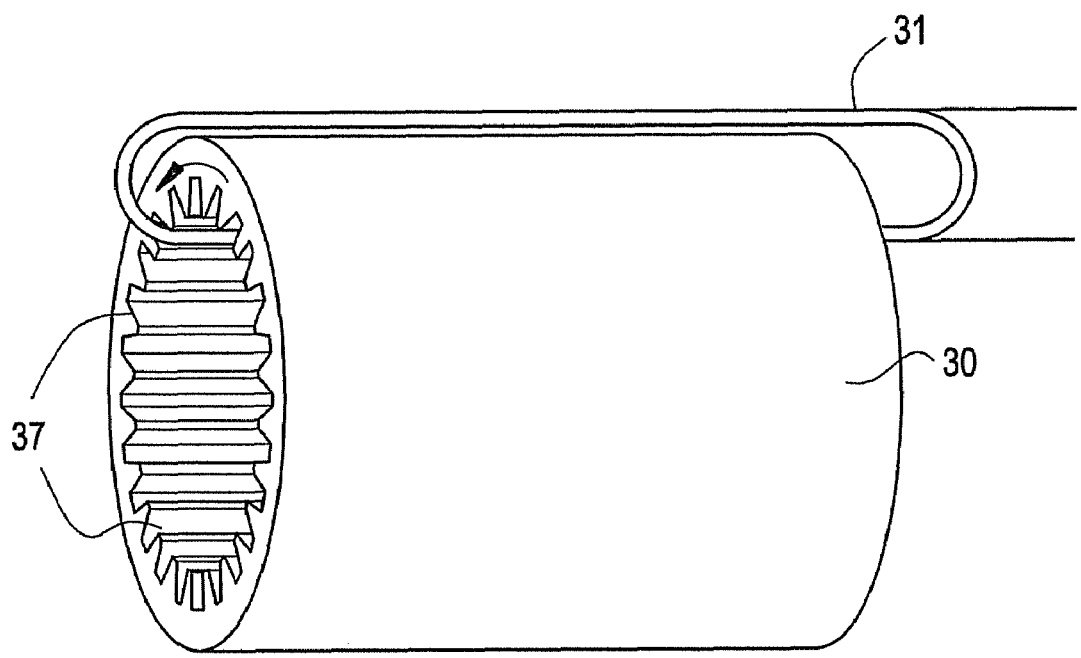
FIG. 1 is perspective schematic view of a conventional stator core for which the embodiments of the sensor arrangement are applicable.
Figure 2:
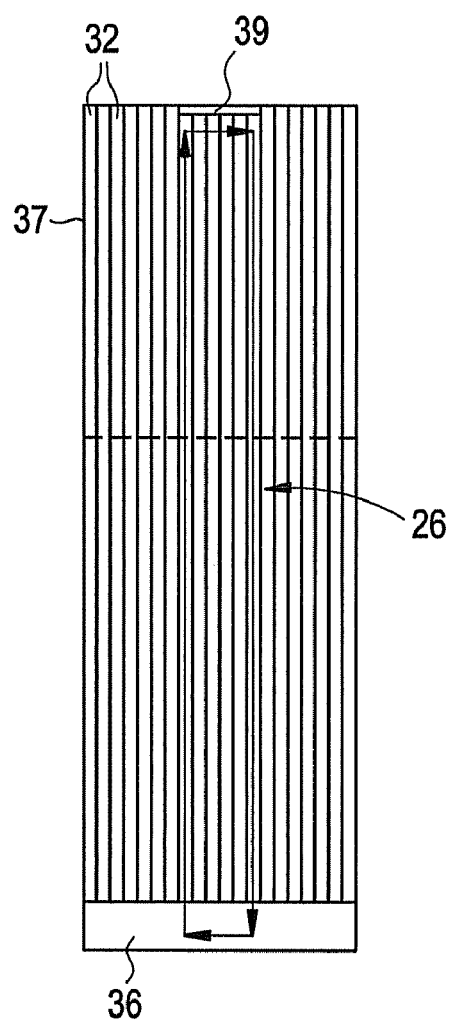
FIGS. 2 and 3 are side and front views, respectively, of stator laminations depicting the manner in which the stator core is constructed from a plurality of thin insulated steel laminations, which are connected to a frame of the stator by way of dovetail grooves and key bars.
Figure 3:
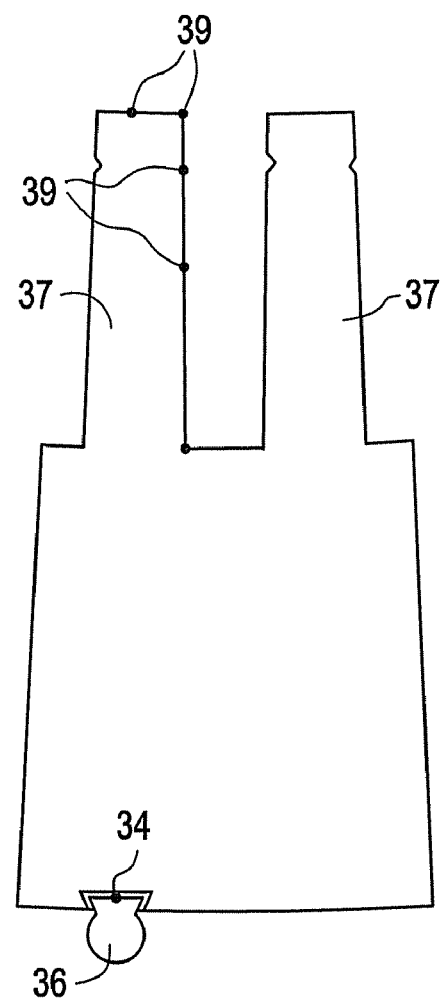
Figure 4:
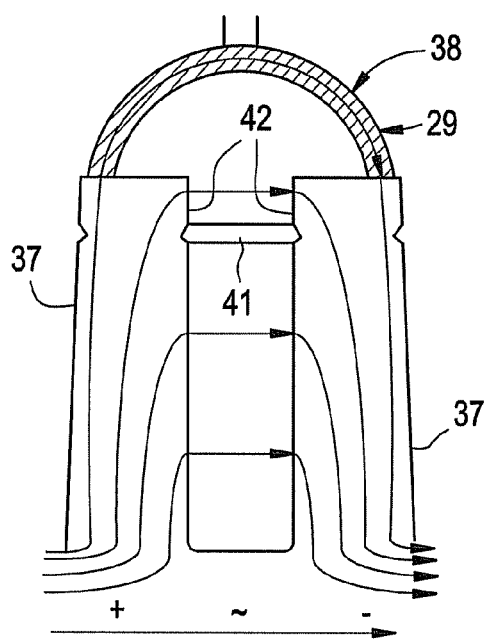
FIG. 4 is a schematic front view of two stator teeth which are being examined using an EL CID type sensor arrangement and which depicts the leakage flux, which is produced when there is no fault associated with the teeth.
Figure 5:
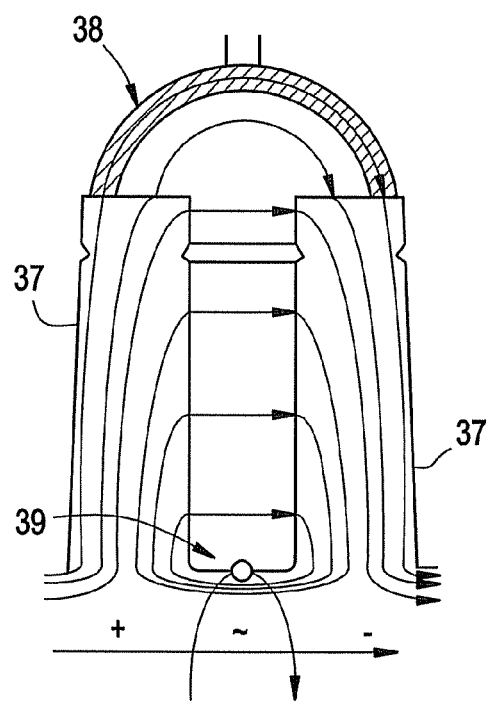
FIG. 5 is a schematic front view of two stator teeth which are being examined using the EL CID type sensor arrangement and which depicts the leakage flux, which is produced when there is a fault associated with the teeth.
Figure 6:
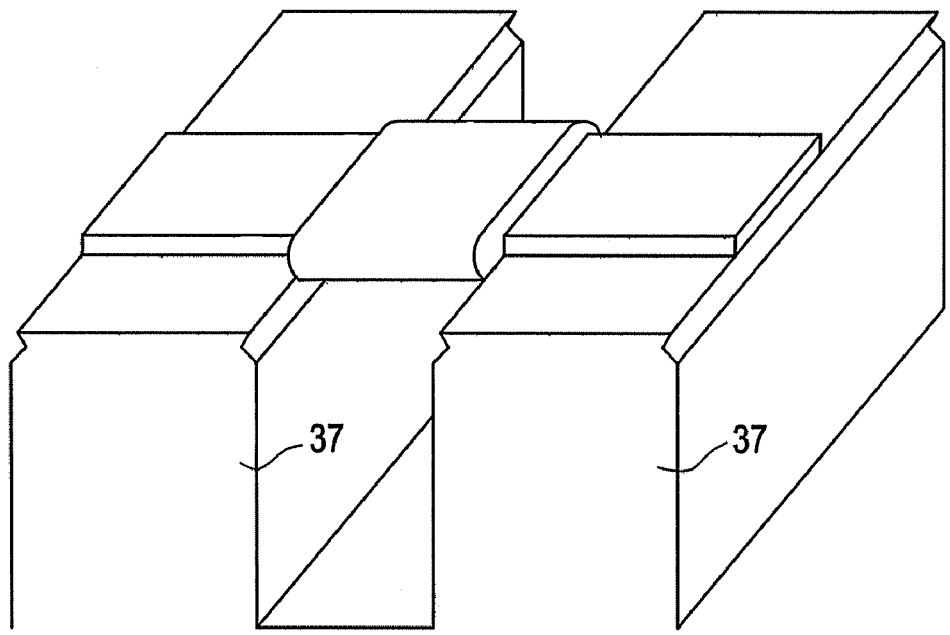
FIG. 6 is a perspective view showing a RU 2082274 C1 prior art sensor arrangement referred to in the opening paragraphs of this disclosure.
Figure 7:
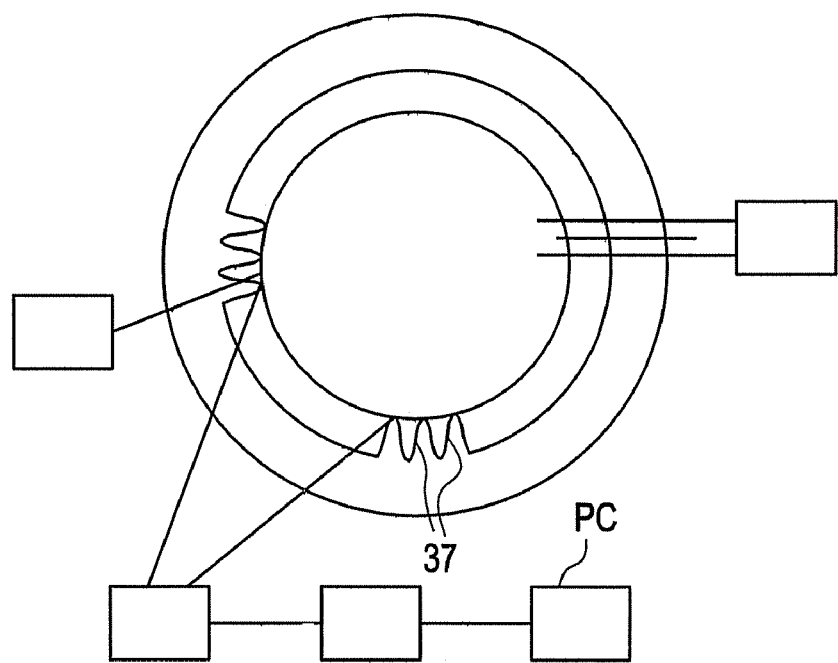
FIG. 7 is a schematic view showing the manner in which the two sensors, which are used with the RU 2082274 C1 arrangement, are deployed in a stator core along with the circuitry associated with the testing procedure.
Figure 8:
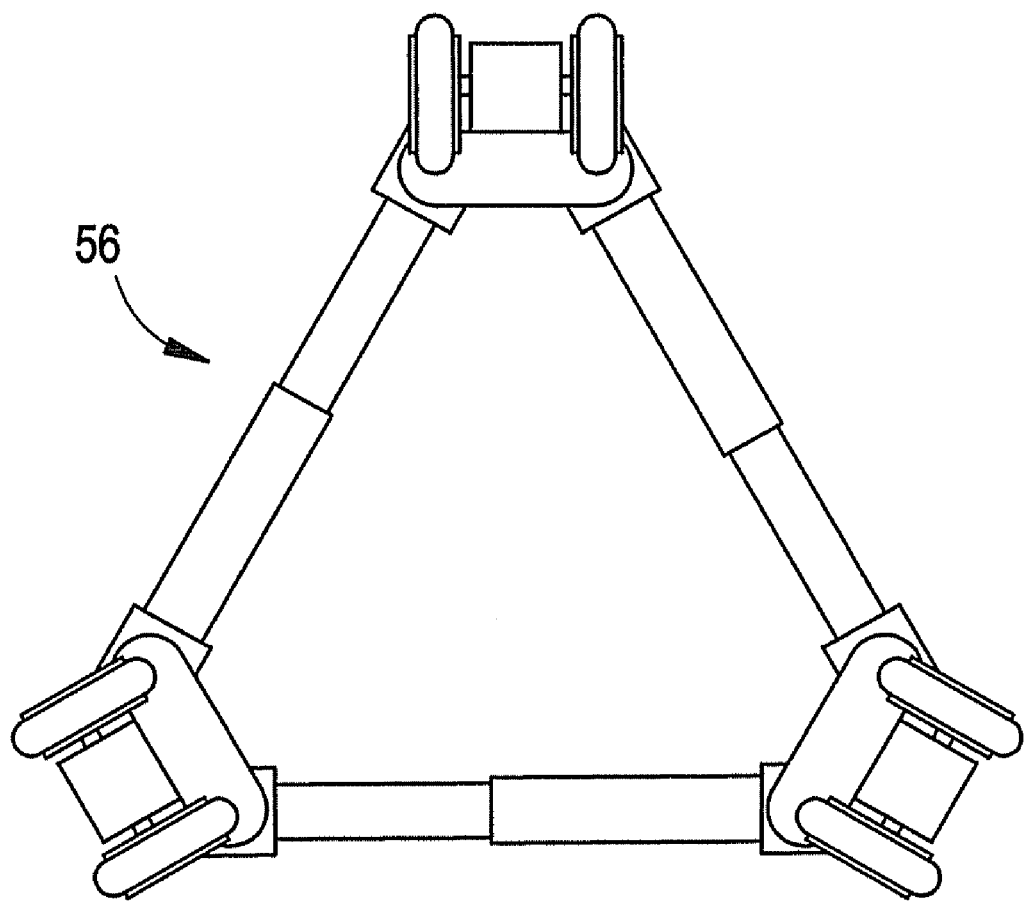
FIG. 8 is a prior art carriage arrangement which is used in connection with the sensors of FIG. 7 and which is disclosed in the RU 2082274 C1 arrangement.

In brief, a disclosed embodiment of the invention comprises a probe that includes a core and a sense coil surrounding the core. The core is disposed in a contact-free, spaced relationship between opposed surfaces 42 of the device being probed. The opposed surfaces 42 are, for example, the sidewalls of adjacent lamination teeth 37 of a stator core 30. Small air gaps are carefully maintained between the ends of the core and the opposed surfaces 42. The effects of probe position are minimized since the net gap is constant. The probe is supported on a carriage arrangement and moved along between the teeth 37. Variations in a leakage flux 29 produced with the stator energized are monitored. The stator is energized with an energization winding to a few percent of a normal energization level. Detection of an abnormal leakage flux indicates the presence of a fault.

FIGS. 9–13 show an exemplary embodiment of the invention. In this arrangement, the sensor or probe 100 consists of a ferromagnetic sense core 102 that is disposed through a sense coil 104. The sense coil 104 is connected with a circuit arrangement 106 of the nature schematically depicted in FIG. 13. The sense core 102 is located with respect to the laminated teeth 37 so that air gaps 108, 109 (best seen in FIG. 11) are defined between the opposed surfaces 42 of the adjacent teeth 37 between which the probe 100 is disposed, and the respective opposing ends defining the sense core 102.

This probe arrangement provides enhanced versatility and reliability with which faults can be detected, reduces scan time, and is easy to handle. The basic principle of low level stator core excitation is similar to that of the above-mentioned EL CID, but an iron core probe is used for sensing the signals between the opposed surfaces 42 of the device being probed.

The use of a probe 100 having a core formed of a magnetic material results in a significant increase in the signal level since the probe 100 provides a low magnetic reluctance path for the magnetic flux. The measured probe voltage is 2–3 orders of magnitude higher than that of an air core probe, such as a Chattock coil 38, due to the high flux concentration in the probe, resulting in improved signal to noise ratio of the voltage measurement. The probe is disposed between the opposed surfaces 42 with a total air gap of up to about 0.5 cm on either side of the probe 100. Maintaining these air gaps is important to minimize noise being introduced into the output of the probe 100.

Excitation System

Figure 13:
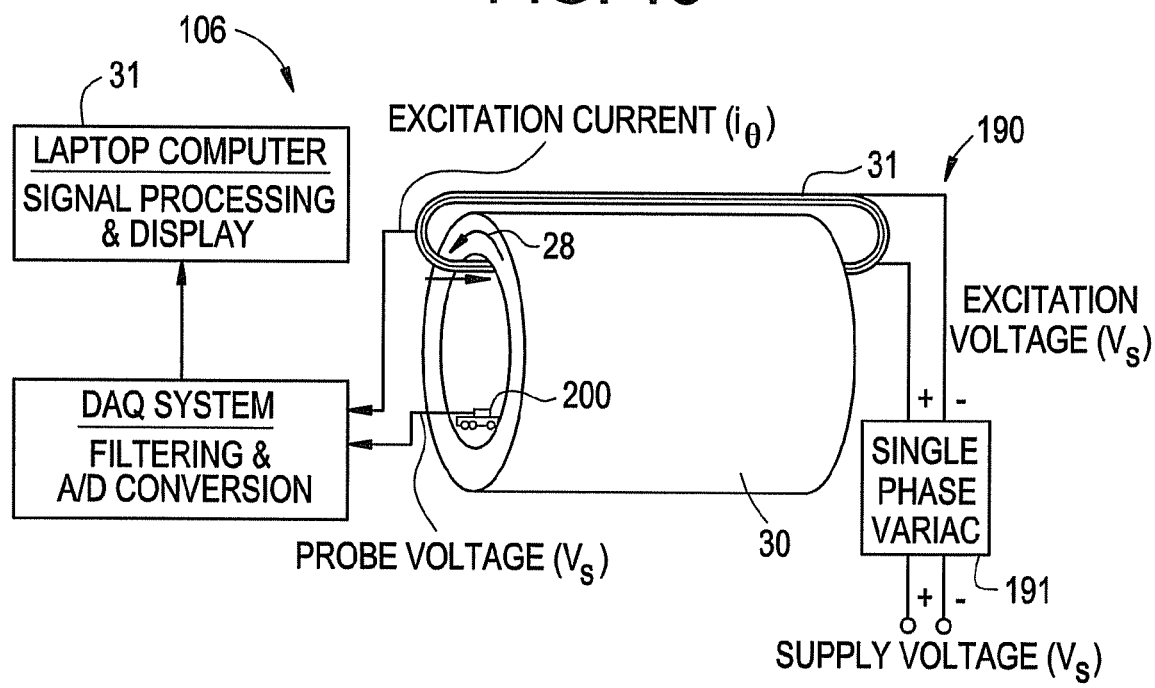
FIG. 13 is a diagram showing an example of a circuit arrangement, which can be used in conjunction with the sensor/probe arrangement of FIG. 9 to detect the fluctuation in leakage flux.

The stator core 30 is, as shown in FIG. 13, operatively connected with an excitation system 190. This excitation system 190 provides a circulating magnetic flux in the yoke of the stator core for fault current 26 excitation. The excitation system 190 comprises a single phase variable auto transformer 191 and an excitation winding 31. The excitation system 190 may comprise a 120/240V single phase variable auto transformer connected to the excitation winding. Alternatively, a single phase variable auto transformer and a cable with at least 20A current conducting capability can also be used to excite the core.

A software program run in a personal computer (PC), which forms part of the circuit arrangement 106, calculates and displays the number of excitation winding turns (2–7) and the excitation voltage that produces a desirable magnetic flux in the core. In order to conduct an example examination, the excitation flux 28 can, for example, be controlled to about 0.075 T (3–4% of rated flux) and the excitation frequency can be controlled to be about 50/60 Hz. However, this embodiment of the invention is not limited to these parameters and various others can be used without departing from the scope of the invention.

In accordance with this embodiment of the invention, the calculation of the excitation voltage and number of excitation winding turns is based on the dimensions of the generator stator core 30. The parameters for calculation of the voltage and number of turns, examples of which are listed below, are those required for calculating the effective area for the circulating flux.

1) Inner Diameter/Radius (ID/IR (in))
2) Outer Diameter Radius (OD/OR (in))
3) Tooth length (TL (in))
4) Core Length (CL (in))

All of the parameters can be obtained from the generator design sheets or easily measured. The effective core length can be assumed to be approximately 10–90% of the core length unless otherwise specified since the inside space block and insulation must be taken into account.

Figure 14:
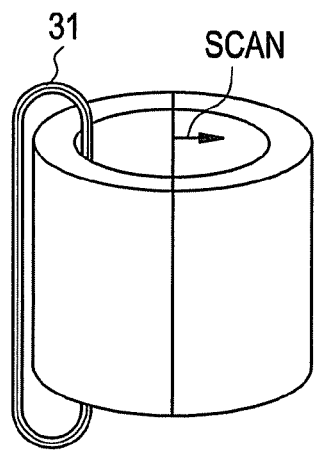
FIGS. 14 and 15 are schematic depictions of stators, which demonstrate how the excitation coil can be disposed with respect to sensor position to reduce noise during examination of the stator.
Figure 15:
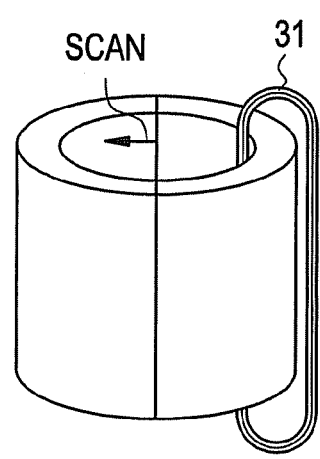

It has been observed in field testing that scanning in a slot near the excitation winding 31 or when internal lighting is used, the noise distorts the signals obtained from the probe due to interference. Therefore, it is recommended that all of the lighting (or the like type of electrical equipment) should be removed, and that the excitation winding 31 should be moved to the opposite side of the stator core 30 from the side being scanned at least once during scanning, as shown in FIGS. 14 and 15, so as to be distant from the probe and thus facilitate accurate measurements.

Probe Carriage System

Figure 11:
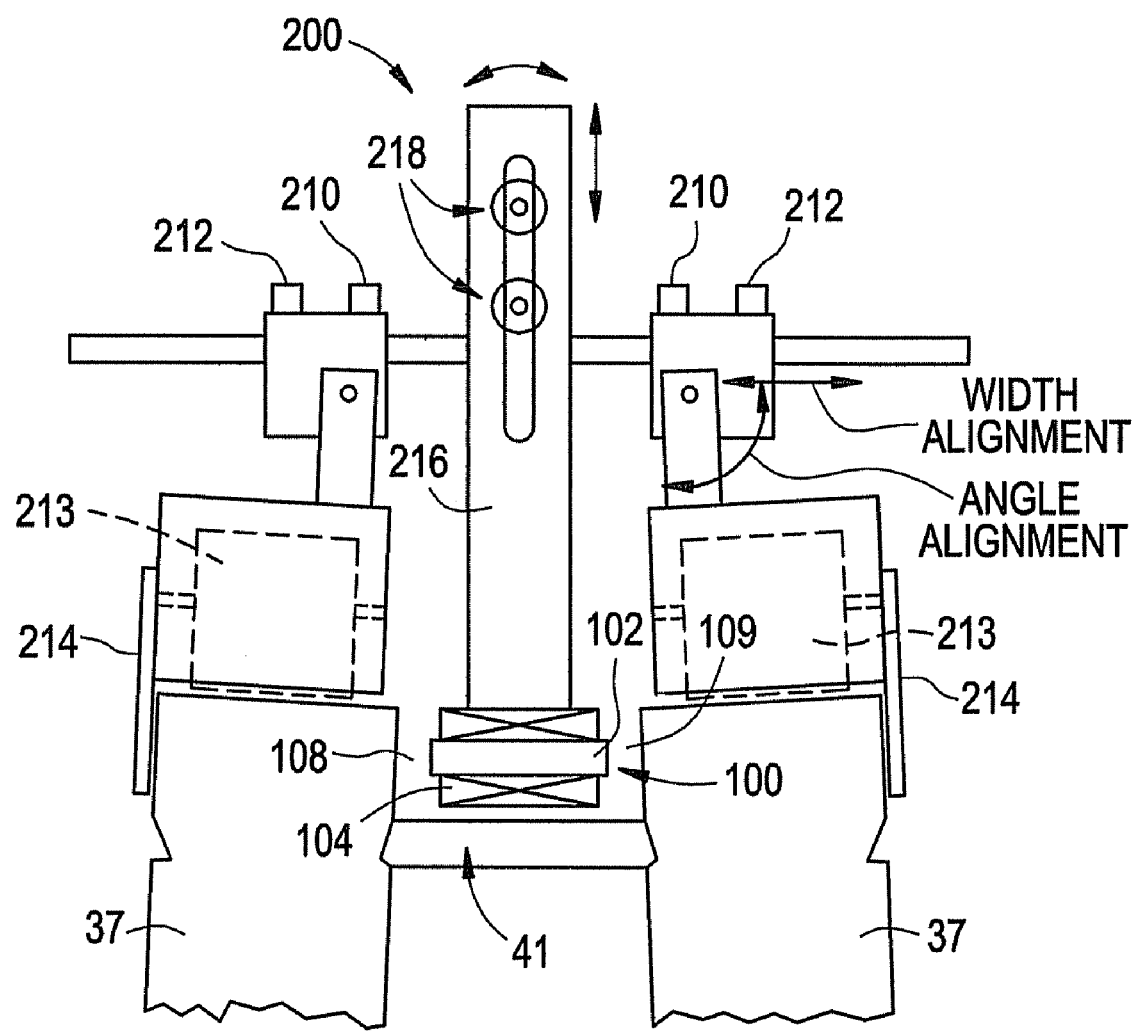
FIG. 11 is a schematic front view showing an example of a carriage arrangement, which can be used to support and move the sensor/probe arrangement of FIG. 9 in accordance with the preferred embodiments of the present invention.
Figure 12:
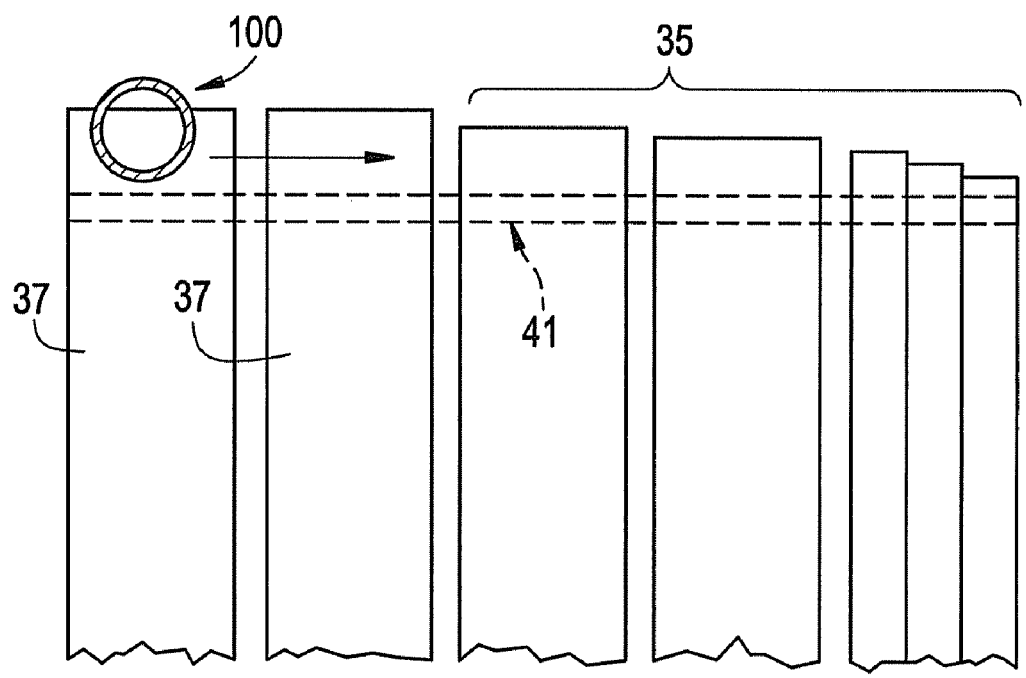
FIG. 12 is a schematic view showing the sensor being moved through a stator toward the end step region where the length of the teeth is reduced.
Figure 24:
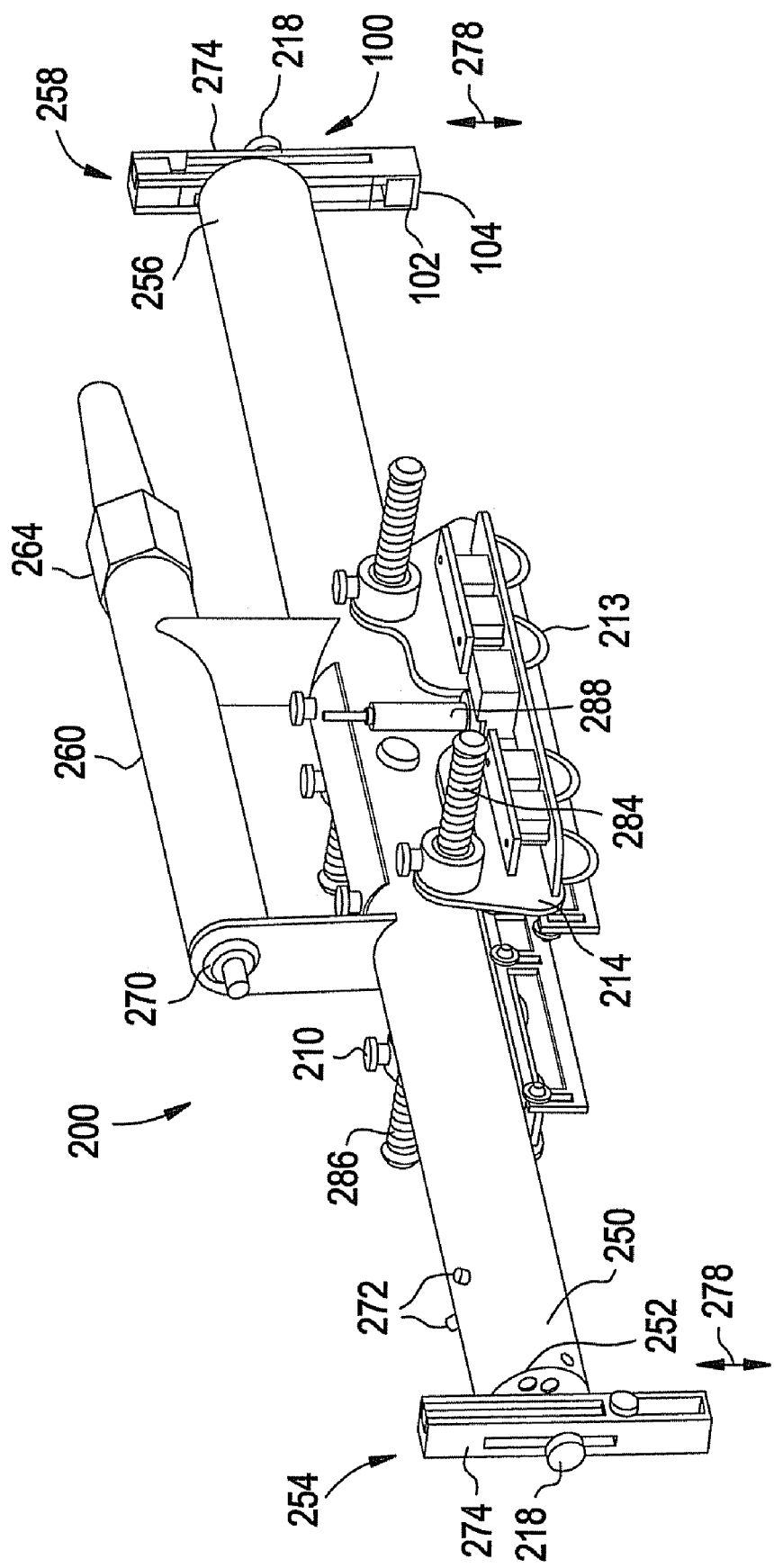
FIG. 24 is a similar and more detailed view of the carriage arrangement that is shown in FIG. 11, which can be used to support and move the sensor/probe arrangement.

In order to facilitate scanning, the probe 100 is supported on a carriage system. An example of a carriage system is shown in FIGS. 11 and 24. In this arrangement the carriage system is a trolley 200 designed to suspend the probe 100 in the proper position when scanning in the axial direction. Proper positioning and alignment of 1) the trolley 200 to the generator teeth 37 and 2) the probe 100 to the trolley 200 are important for obtaining accurate measurements.

Selecting a proper width of the probe 100 is a trade off between signal level and ease of scanning. Increasing the probe 100 width (viz., decreasing the air gaps 108 and 109) increases the signal level, but also increases the chance of contact between the probe core 102 and teeth 37 between which it is disposed. Contact, of course, causes the signal to be noisy. The probe width, which has been experimentally shown to ensure good signal measurement and ease of scanning (no contact), is approximately the slot width minus about 0.38 cm to about 0.5 cm. For example, if the slot thickness is 3.266 cm, an appropriately sized probe 100 would be anywhere between about 2.8 cm to about 2.9 cm wide.

The width and angle of trolley wheels 213 can, as shown in FIG. 11, be adjusted by rotating corresponding adjustment screws 210, 212 so that the trolley guidance plates 214 fit flush and snug against the outboard sides of the teeth 37, between which the probe 100 is suspended, to prevent tilting of the trolley. The probe 100 is securely attached to a probe extension piece 216 to avoid tilting and inconsistent measurement data.

Once the probe 100 is attached to the probe extension 216, the probe 100 is located between the opposed surfaces 42 of the device as shown in FIG. 11 by adjusting two probe location adjustment screws 218. Loosening probe location adjustment screws 218 permits adjustment of the probe 100 in the vertical direction. Tightening probe location adjustment screws 218 fixes the probe 100 at a selected position. It is desirable that steel parts of the probe 100 be located midway between the opposed surfaces 42 and slightly above the slot wedge 41.

Data Acquisition System

The two measurements which are taken in accordance with this embodiment of the invention are probe voltage and excitation current. These parameters can be measured using commercially available hardware, such as a Wavebook® 516 portable data acquisition (DAQ) system marketed by IOTECH®.

The software program controls the settings of the data acquisition system and also processes, displays, and stores the data acquired from the scanning of each slot. The software provides a parameter input screen and a main program screen. The parameter input screen allows an operator to enter information including test parameters and generator dimensions. The number of excitation winding 31 turns and excitation voltage are calculated and displayed based on the information entered into the software. The main program screen displays the measured and processed signals.

Interpretation of Results

Figure 16:
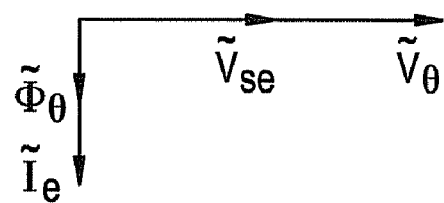
FIG. 16 is an example of a phasor diagram showing characteristics, which are obtained with a fault free or healthy core system.
Figure 18:
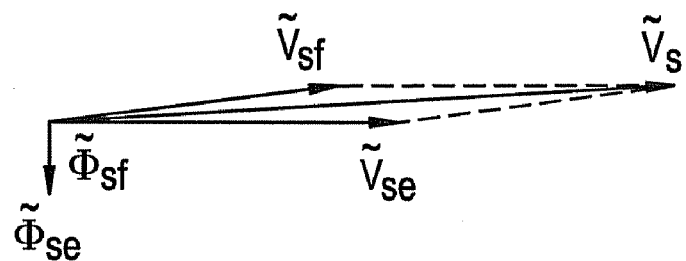
FIG. 18 is an example of a phasor diagram, which is produced when a sub-wedge fault condition is detected.

A phasor diagram is used to indicate the status of the inter-laminar core fault system. Examples of such a phasor diagrams are shown in FIGS. 16 and 18. In this system, $V_e$, $I_e$, and $\phi_e$ represent the excitation voltage, current, and flux, respectively. $V_s$, $V_{se}$ are the measured probe voltage and probe voltage due to the excitation. For properly manufactured, defect-free (healthy) laminations, $V_s$ and $V_{se}$ are equal, as depicted in FIGS. 16 and 18.

Figure 17:
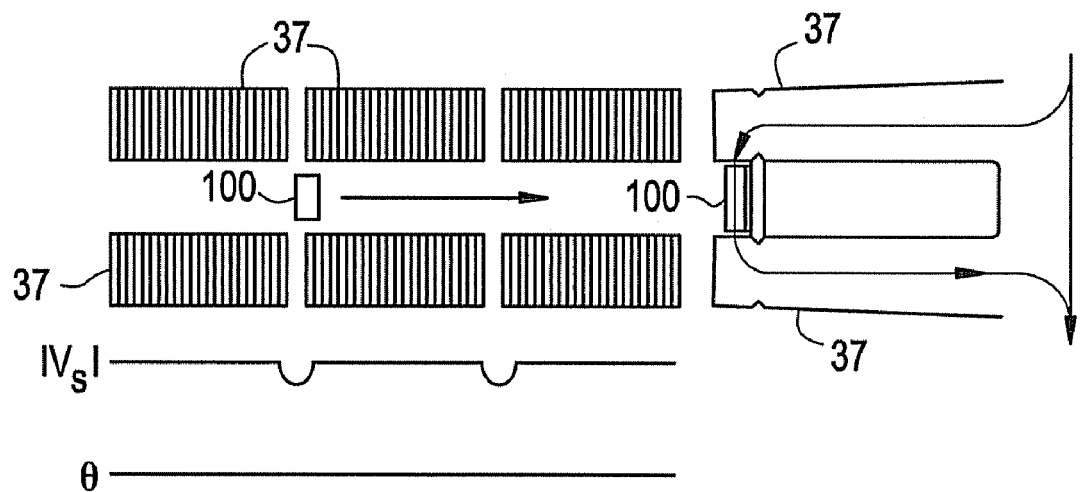
FIG. 17 is a compound schematic diagram depicting sensor position and signals, which are obtained with a healthy lamination arrangement.

The software displays the magnitude of the measured probe voltage in RMS, $V_s$, and the phase angle between the probe voltage and the derivative of the excitation current, $\theta$. Both signals are calculated based on the measured probe voltage and current, and both signals are taken into account to determine the existence, severity, and location of the fault. For healthy laminations, the ideal measured signals and flux distribution are shown in FIG. 17. The dips in the voltage magnitude $|V_s|$ are caused by the inside space blocks. The voltage magnitude is constant except when passing the inside space blocks and the angle is constant throughout the scan. The dips corresponding to the inside space blocks can be counted to estimate the approximate location of the fault when a suspicious signal is found.

When a fault is present inside the slot, the flux distribution changes since the voltage induced in the fault, $V_f$, causes a fault current flow, $I_f$, which induces an additional fault flux component, $\phi_f$, which changes the flux going through the probe 100. The phasor diagram under a sub-wedge fault condition is shown in FIG. 18, where $V_{sf}$ is the measured probe voltage component due to the fault, and $V_s$ is the measured probe voltage.

Figure 19:
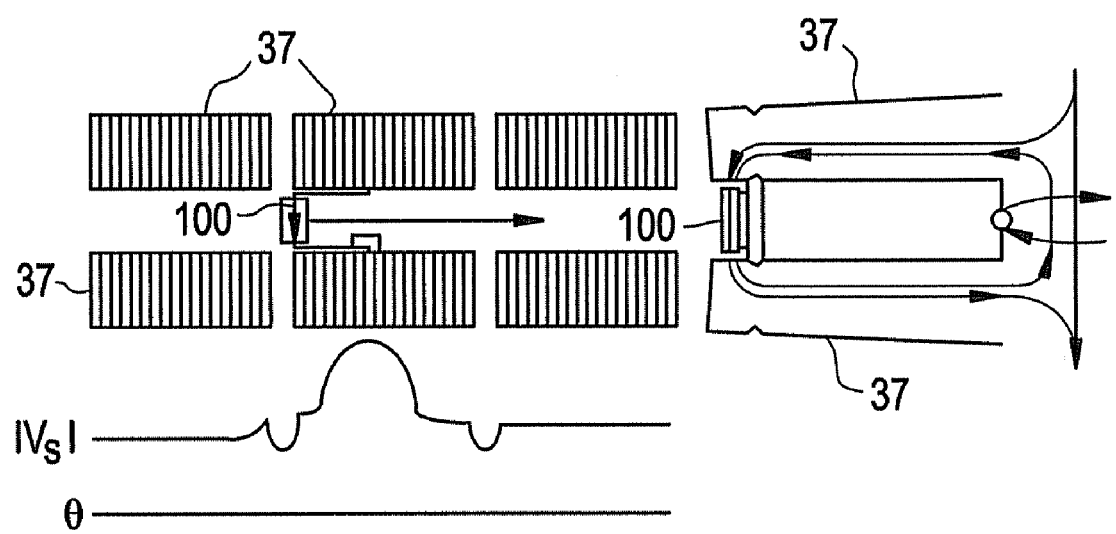
FIG. 19 is a compound schematic diagram depicting sensor position and signals, which are obtained when a sub-wedge fault condition is detected.

The measured probe voltage $V_s$ can be assumed as a phasor sum of the voltage component induced due to the excitation flux 28 and the fault flux, as shown in FIG. 18, which results from a sub-wedge fault. The typical waveform and flux distribution under this fault condition are as shown in FIG. 19. It can be seen in FIG. 19 that the magnitude change (i.e. increase) in the measured probe voltage $V_s$ is noticeable under this fault condition, but the phase angle change is very small. The fault signatures are similar when the faults are between the slot wedge 41 dovetail and the tooth 37 root.

Figure 20:
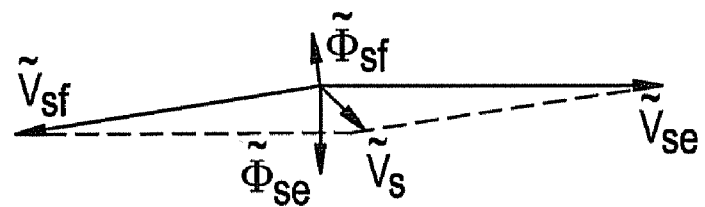
FIG. 20 is an example of a phasor diagram which is produced when a surface fault condition is detected.
Figure 21:
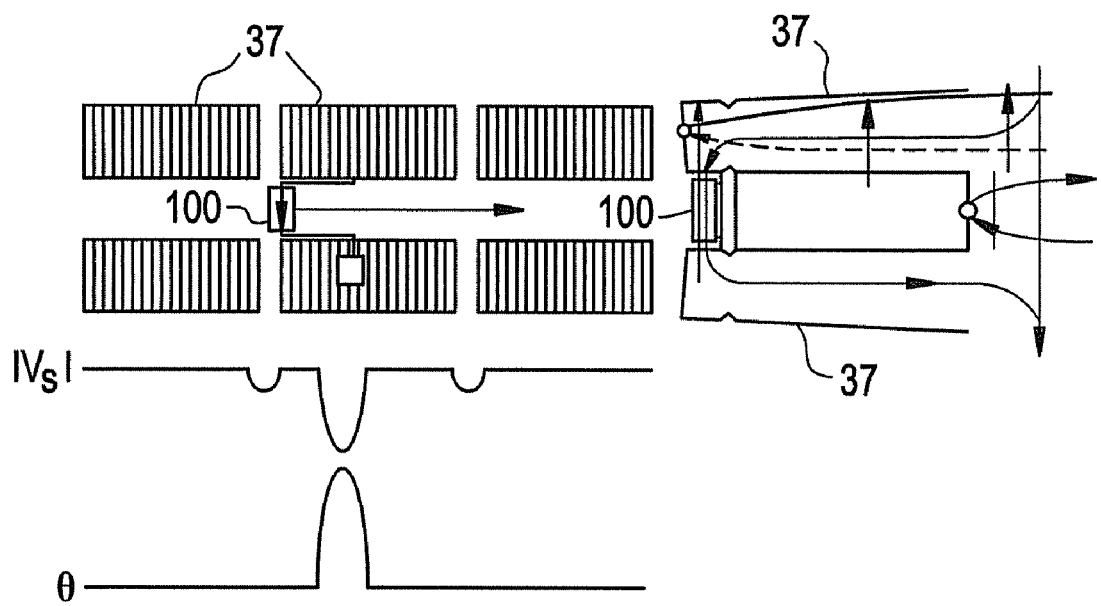
FIG. 21 is a compound schematic diagram depicting sensor position and the signals which are obtained in the presence of a surface fault condition.

The phasor diagram under a surface fault condition (e.g., fault on a tooth tip) is shown in FIG. 20. The main difference between a surface fault and a sub-wedge fault is that the fault flux in the probe opposes the excitation flux 28 as shown in FIG. 21. As a result, the probe voltage magnitude decreases and the phase angle changes significantly.

As will be appreciated from the above examples, the existence of a fault can be determined by any deviation from a healthy signature. The location of the fault can be determined based on the magnitude and phase angle signatures. It has been observed that both the magnitude and phase angle change increase with the severity of faults.

Figure 22:
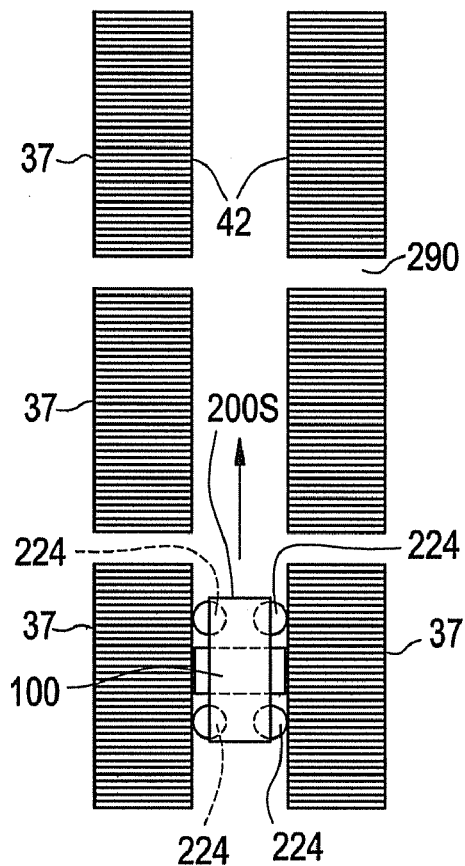
FIGS. 22 and 23 are plan and front views, respectively, showing an alternative embodiment of a carriage arrangement, which can be used to support and move the sensor/probe arrangement.
Figure 23:
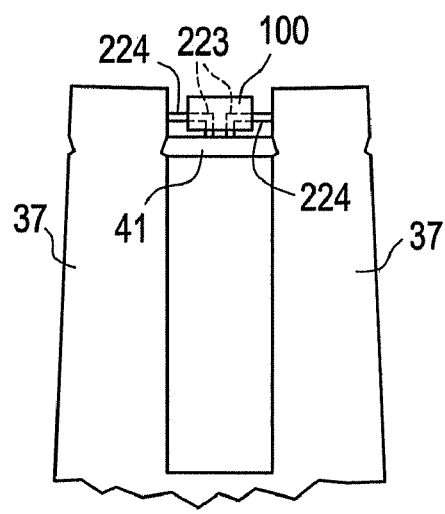

As an alternative to the disclosed probe trolley arrangement it is possible to arrange a trolley or a small robotic vehicle to run along the top of the slot wedge 41 in the manner schematically depicted in FIGS. 22 and 23. The trolley or vehicle 300, in this instance, is supported on rollers 223 and is also provided with side rollers 224, which roll along the inboard faces of the teeth 37 between which the probe 100 is disposed. The rollers 223 can be adjusted to accommodate a change in a slot width. The side rollers 224 can be spring loaded to allow automatic adjustment for differently spaced teeth 37. The length of the probe core can be rendered adjustable.

This trolley arrangement can be rendered to be totally robotic and provided with its own independent power source (e.g., batteries) and with a transmitter to relay sensed flux data to a remote station. By transmitting in a suitable frequency range, the data can be transmitted to the remote station without being affected by noise or the like.

FIG. 24 is a similar and more detailed view of the trolley 200, which is illustrated in FIG. 11. Referring to FIGS. 11 and 24, the trolley 200 includes a body 250, which in an exemplary embodiment is a tubular body. The body 250 facilitates the storage of the wires (not shown) for the probe system. It is understood that the body 250 may be any shape that facilitates storage of the wires. Body 250 has a first end 252 with a first probe extension piece 254 for mounting a first probe 100. Body 250 also has a second end 256 with a second probe extension piece 258 for mounting a second probe 100. Body 250 includes a handle 260 to facilitate manual control of the trolley 200. At an end 262 of handle 260, there is a strain relief 264, which stores the wires for the probe system and allows connection to a cable (not shown). Handle 260 includes a switch 270 for manually turning probe system on and off. By having switch 270 on the trolley 200, a reading can be accomplished by one technician. Body 250 also includes indicator lights 272, which indicate when the probe 100 is in standby mode and when the probe 100 is recording.

Probe extension pieces 254 and 258 each include a probe bracket 274 and an adjusting screw 218 for adjusting probe 100 in a vertical direction 278. Iron core 102 is positioned into a slot in bracket 274 and is secured to bracket 274 using an epoxy, for example. Positioning the iron core 102 in this way allows the probe 100 to be securely attached to the probe extension pieces 254 and 258, which helps to avoid tilting that causes inconsistent measurement data. The slot is a fixed size and the sense core 102 can vary in length from about 1 cm to about 7.6 cm. A length of the sense core 102 is chosen depending on characteristics of a device being probed. While the trolley 200 only requires one probe 100 for operation, this trolley 200 includes two probes 100 so that the trolley 200 does not have to be flipped or maneuvered to cover the end step region 35 (see FIG. 12).

Trolley 200 includes trolley wheels 213 that can be adjusted by rotating the corresponding adjustment screw 210 so that trolley guidance plates 214 fit flush and snug against the inboard sides of the teeth 37 between which the probe 100 is suspended to prevent tilting of the trolley 200. Trolley wheels 213 are disposed in pairs on a width-adjusting member 284. Width-adjusting member 284 is disposed substantially perpendicular to a longitudinal axis of the trolley 200 and extends from opposite sides of the body 250 in a direction substantially parallel to a top surface of the teeth 37 on which the trolley 200 is supported. Trolley wheels 213 are disposed at the width-adjusting member 284 such that a wheel of each pair of wheels is located on opposite sides of the body 250. Adjustment screw 210 is rotated to allow trolley wheels 213 to be positioned apart from one another at a predetermined width corresponding to a distance between selected teeth 37. When adjustment screw 210 is tightened, trolley wheels 213 are secured in place by notches 286 disposed on an upper surface of the width-adjusting member 284. Although trolley wheels 213 are used to move the trolley 200 in an exemplary embodiment, one skilled in the art will recognize that other means of transporting and supporting the trolley 200 may be employed, such as, for example, bearings, rollers, tracks, etc.

Trolley 200 also includes an inductive sensor 288. An exemplary embodiment of an inductive sensor 288 is an eddy current type sensor though use of other suitable sensors is envisioned. Inductive sensor 288 is capable of distinguishing between air and metal, thus inductive sensor 288 senses a ventilation space 290 (see FIG. 22) between consecutive teeth 37. Inductive sensor 288 counts a number of ventilation spaces 290 to reliably determine axial position of the probe 100 inside the stator core 30. Thus, a slipping of the trolley wheels 213 causes no accumulative errors in determining position of trolley 200 along an axis of the device being probed.

Once each probe 100 is attached to the corresponding probe extension pieces 254 and 258, the probe 100 is located between the opposed surfaces 42 of the device as shown in FIG. 11 by adjusting the probe location adjustment screw 218. It is desirable that steel parts of the probe 100 be located at the center of the slot and slightly above the slot wedge 41.

The probe 100 is not limited to structures that are totally enclosed by the sidewalls of the teeth 37. The coil 104 and other parts of the probe 100 can be configured as desired and located above the level of the teeth 37 while suitable extensions of the sense core 102 project down into the space defined between the sidewalls of the teeth 37 and thus establish the air gaps 108 and 109.

The sense core 102 of the probe, which is solid, is different from an air core such as used in the EL CID sensor arrangement. The sense core 102 is preferably made of a material which is easy to work with, such that it is neither too hard, nor too soft, nor difficult to shape, and which exhibits high initial permeability under low flux along with high resistivity characteristics. The sense core 102 can be made of a composite material, a suitable single material such as a metal, or formed of laminations that are secured together. For example, a suitable steel can be used and plates of this type of material (or a mixture of plates of different materials) can be bonded together in order to achieve both the desired shape and durability as well as the above mentioned high initial permeability under low flux and high resistivity characteristics. The sense core 102 can be configured into any suitable configuration and is not limited to the illustrated shape that has been depicted as being essentially cylindrical for illustrative simplicity.

The probe 100 is not limited to the use of a single core or a single coil and multiple cores and coils can be used. All cores need not pass through a coil and the arrangement which enables the required sensitivity of the flux in the air gaps 108 and 109 is within the purview of the invention. The coils per se of the probe need not be disposed between the teeth 37 and the core can be configured to extend sensing portions thereof into the space between adjacent teeth 37 and establish the necessary sensing portion-air gap relationship.

It should be noted that the air gaps 108 and 109 need not be equal and that a limited amount of movement of the probe 100 with respect to the sides of the teeth 37 is therefore possible. Given that the total of the air gaps 108 and 109 remains constant and no direct contact between the ends of the core and the teeth 37 occurs, accurate flux detection results are possible.

In addition, while the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A probe support carriage for use during probing an electrical device, comprising:
   a body having a first end and a second end;
   means for supporting and positioning said body;
   a plurality of flux sensors operatively connected to and extending from said body via a plurality of probe extension pieces, each flux sensor of said plurality of flux sensors comprising a probe having a core structure of a material having high initial permeability and high resistivity characteristics, and a coil structure separate from said core structure and disposed with said core structure, said probe adapted to being supported so that a sensing portion of said core structure is maintained in a contact-free spaced relationship between a predetermined surface of the electrical device and said sensing portion of said core structure; and
   a position sensor adapted to determine position along a longitudinal axis of the electrical device.

2. The probe support carriage of claim 1, wherein said each flux sensor is moved through the electrical device to scan the electrical device for a fault which produces a change in a leakage flux.

3. The probe support carriage of claim 1, wherein one extension piece of said plurality of extension pieces connecting one of said plurality of flux sensors to said body is disposed at said first end of said body and another extension piece of said plurality of extension pieces connecting another of said plurality of flux sensors to said body is disposed at said second end of said body allowing an entirety of said predetermined surface of the electrical device to be scanned without flipping the probe support carriage.

4. The probe support carriage of claim 1, wherein said each flux sensor is receptive to a vertical adjustment to position said each flux sensor at a predetermined distance from said predetermined surface of the electrical device.

5. The probe support carriage of claim 1, wherein said core structure in said each flux sensor at least partially comprises an iron.

6. The probe support carriage of claim 5, wherein said core structure varies in length from about 1 cm to about 7.6 cm based on a characteristic of the electrical device.

7. The probe support carriage of claim 1, wherein said predetermined surface comprises opposed surfaces of the electrical device, said leakage flux passes between said opposed surfaces and through an air gap defined between said opposed surfaces and said sensing portion of said core structure.

8. The probe support carriage of claim 1, wherein said means for supporting and positioning said body comprises wheels.

9. The probe support carriage of claim 8, wherein said wheels are disposed near a bottom portion of said body and said wheels comprise at least a wheel disposed on each side of a longitudinal centerline of said body.

10. The probe support carriage of claim 9, wherein a width between said wheels is adjustable.

11. The probe support carriage of claim 10, wherein said width between said wheels is selected to span a distance between said opposed surfaces.

12. The probe support carriage of claim 10, wherein an axle of said wheels is in mechanical communication with a guidance plate, said guidance plate is disposed in communication with at least one of inboard sidewalls of said predetermined surface and outboard sidewalls of said predetermined surface to prevent tilting of said body.

13. The probe support carriage of claim 1, wherein said position sensor comprises an inductive sensor.

14. The probe support carriage of claim 13, wherein said inductive sensor is an eddy current type sensor adapted to distinguishing air from metal, said inductive sensor is able to sense a ventilation space of said predetermined surface.

15. The probe support carriage of claim 14, wherein said inductive sensor counts a plurality of ventilation spaces to determine position along said axis of the electrical device.

16. The probe support carriage of claim 1, wherein said body includes a light assembly adapted to indicate a status of said each flux sensor.

17. A method of detecting an electrical fault in an electrical device comprising:

extending plurality of probes from a trolley via a plurality extension pieces, each probe of said plurality of probes having a solid core structure and a coil structure separate from said solid core structure and disposed with said solid core structure;

maintaining a sensing portion of said solid core structure in a contact-free, spaced relationship between opposed surfaces of members of the electrical device and through which a leakage flux passes;

inducing energization of the electrical device to a predetermined level which is lower than a normal operating level and thus produce said leakage flux;

detecting said leakage flux using said each probe at a first position;

moving said trolley to a second position with respect to said opposed surfaces and detecting said leakage flux at said second position;

monitoring a fluctuation in output of said each probe and detecting the fault in response to an abnormal leakage flux; and determining an axial position of said trolley within the electrical device.

18. The method of claim 17, further comprising:

disposing a first extension piece of said plurality of extension pieces at a first end of said trolley, said first extension piece connecting a first probe of said plurality of probes to said first end of said trolly; and disposing a second extension piece of said plurality of extension pieces at a second end of said trolley, said second extension piece connecting a second probe of said plurality of probes to said second end of said trolly.

19. The method of claim 17, wherein said determining said axial position further comprises:

sensing a difference between a metal surface and a ventilation space on said opposed surfaces of the electrical device; and counting a number of a plurality of said ventilation spaces.

20. The method of claim 17, wherein said inducing energization of the electrical device comprises inducing energization of less than about 4% of said normal operating level.

* * * * *